United States Patent [19]

Führer et al.

[11] Patent Number: 4,610,985
[45] Date of Patent: Sep. 9, 1986

[54] ALLOPHANATE DERIVATIVE, FUNGICIDAL COMPOSITIONS AND USE

[75] Inventors: Wolfgang Führer, Hennef; Engelbert Kühle, Bergisch-Gladbach; Gerd Hänssler, Leverkusen, all of Fed. Rep. of Germany

[73] Assignee: Bayer Aktiengesellschaft, Leverkusen, Fed. Rep. of Germany

[21] Appl. No.: 721,738

[22] Filed: Apr. 10, 1985

[30] Foreign Application Priority Data

Apr. 19, 1984 [DE] Fed. Rep. of Germany ....... 3414881

[51] Int. Cl.[4] .................. A01N 47/20; C07C 125/065; C07C 125/067; C07D 295/20
[52] U.S. Cl. ....................... 514/235; 558/417; 514/212; 514/330; 514/423; 514/479; 514/482; 514/232; 544/163; 544/165; 544/167; 546/205; 546/206; 546/226; 548/538; 540/607; 560/22; 560/24; 560/28; 560/29; 560/30; 560/31; 560/32; 560/33
[58] Field of Search ....................... 544/163, 165, 167; 546/205, 206, 226; 548/538; 260/239 BF, 465 D; 560/22, 30, 24, 28, 29, 31, 32, 33; 514/212, 235, 330, 423, 479, 482, 232

[56] References Cited

U.S. PATENT DOCUMENTS 3,950,367 4/1976 Botta ..................................... 560/30
4,482,737 11/1981 Kühle et al. .......................... 560/33

OTHER PUBLICATIONS

R. Wegler, Chemistry of the Plant Protection Agents and Agents for Combating Pests, vol. 2, p. 65, Springer Verlag Berlin 1970.

Primary Examiner—Robert W. Ramsuer
Attorney, Agent, or Firm—Sprung Horn Kramer & Woods

[57] ABSTRACT

Allophanate derivatives of the formula

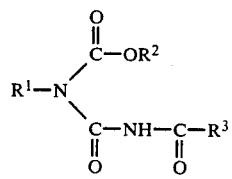

in which $R^1$ and $R^2$ can be identical or different and represent an aliphatic, cycloaliphatic, araliphatic or aromatic radical each of which is optionally monosubstituted or polysubstituted by identical or different substituents and $R^3$ represents the radical $-XR^4$ or $-NR^5R^6$, wherein $R^4$ represents alkyl, alkoxyalkyl, or aryl which is optionally monosubstituted or polysubstituted by identical or different substituents, X represents oxygen or sulphur and $R^5$ and $R^6$ are identical or different and represent hydrogen, alkyl, or aryl which is optionally monosubstituted or polysubstituted by identical or different substituents, or $R^5$ and $R^6$, together with the nitrogen atom on which they stand, form a saturated heterocyclic radical which is optionally monosubstituted or polysubstituted by identical or different substituents and can be interrupted by further hetero-atoms, which possess fungicidal activity.

9 Claims, No Drawings

ALLOPHANATE DERIVATIVE, FUNGICIDAL COMPOSITIONS AND USE

The invention relates to new allophanate derivatives, processes for their preparation and their use as agents for combating pests.

It is already known that various carbonic acid derivatives or metal complexes thereof, for example zinc ethylene-1,2-bis-dithiocarbamate, are suitable for protecting crop plants from attack by harmful fungi [compare, for example, R. Wegler, "Chemie der Pflanzenschutzund Schädlingsbekämpfungsmittel" ["Chemistry of the Plant Protection Agents and Agents for Combating Pests"], volume 2, page 65, Springer Verlag Berlin (1970)].

However, the action of these compounds may not always be satisfactory under certain conditions, for example when low amounts and concentrations are applied.

New allophanate derivatives of the formula (I)

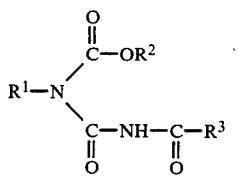

in which $R^1$ and $R^2$ can be identical or different and represent an aliphatic, cycloaliphatic, araliphatic or aromatic radical each of which is optionally monosubstituted or polysubstituted by identical or different substituents and $R^3$ represents the radical $-XR^4$ or $-NR^5R^6$, wherein $R^4$ represents alkyl, alkoxyalkyl, or aryl which is optionally monosubstituted or polysubstituted by identical or different substituents, X represents oxygen or sulphur and $R^5$ and $R^6$ are identical or different and represent hydrogen, alkyl, or aryl which is optionally monosubstituted or polysubstituted by identical or different substituents, or $R^5$ and $R^6$, together with the nitrogen atom on which they stand, form a saturated heterocyclic radical which is optionally monosubstituted or polysubstituted by identical or different substituents and can be interrupted by further hetero-atoms, have been found.

The new allophanate derivatives of the formula (I)

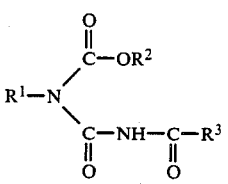

in which $R^1$ and $R^2$ can be identical or different and represent an aliphatic, cycloaliphatic, araliphatic or aromatic radical each of which is optionally monosubstituted or polysubstituted by identical or different substituents and $R^3$ represents the radical $-XR^4$ or $-NR^5R^6$, wherein $R^4$ represents alkyl, alkoxyalkyl, or aryl which is optionally monosubstituted or polysubstituted by identical or different substituents, X represents oxygen or sulphur and $R^5$ and $R^6$ are identical or different and represent hydrogen, alkyl, or aryl which is optionally monosubstituted or polysubstituted by identical or different substituents, or $R^5$ and $R^6$, together with the nitrogen atom on which they stand, form a saturated heterocyclic radical which is optionally monosubstituted or polysubstituted by identical or different substituents and can be interrupted by further hetero-atoms, by a process in which (a) N-isocyanatocarbonyl-carbamates of the formula (II)

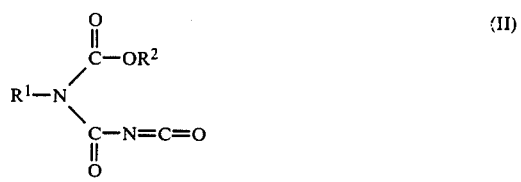

in which $R^1$ and $R^2$ have the abovementioned meaning, are reacted with compounds of the formula (III)

$$MR^3 \quad (III)$$

in which $R^3$ has the abovementioned meaning and

M represents hydrogen or one metal cation equivalent, preferably one alkali metal equivalent, such as sodium or potassium, if appropriate in the presence of a basic auxiliary and if appropriate in the presence of a diluent or solvent, or in which (b) N-halogenocarbonyl-urethanes of the formula (IV)

in which $R^1$ and $R^2$ have the abovementioned meaning and

Hal represents halogen, preferably chlorine, are reacted with compounds of the formula (V)

in which $R^3$ has the abovementioned meaning, if appropriate in the presence of a solvent or diluent and if appropriate in the presence of a base.

The new allophanate derivatives of the formula (I) exhibit, in particular, fungicidal properties. Most of the compounds according to the invention exhibit a more powerful fungicidal activity than the fungicidally active compound already known from the prior art, such as, for example, zinc ethylene-bis-dithiocarbamate. The compounds according to the invention thus represent an enrichment of the art.

Formula (I) provides a general definition of the allophanate derivatives according to the invention.

Preferred compounds of the formula (I) are those in which $R^1$ and $R^2$ are identical or different and represents $C_1$–$C_{10}$-, in particular $C_1$–$C_6$-alkyl, or $C_2$–$C_{10}$-, in particular $C_3$–$C_5$-alkenyl, or $C_2$–$C_{10}$-, in particular $C_3$–$C_5$-alkinyl, optionally substituted by $C_{1-4}$-alkoxy, $C_{1-4}$-alkylthio and/or halogen, preferably fluorine, chlorine, bromine or iodine, in particular fluorine or chlorine, or furthermore represents $C_5$–$C_{10}$, in particular $C_5$- or $C_6$-cycloalkyl, optionally substituted by $C_1$–$C_6$-alkyl, or represents aralkyl with $C_6$–$C_{10}$ in the aryl part and $C_1$–$C_4$, preferably $C_1$–$C_2$ in the alkyl part, optionally substituted in the aryl part by halogen, preferably fluorine, chlorine, bromine, or iodine, in particular fluorine or chlorine, or by nitro, $C_1$–$C_6$-alkyl, cyano and/or trifluoromethyl, or represents $C_6$–$C_{10}$-aryl, optionally substituted by halogen, preferably fluorine, chlorine, bromine or iodine, in particular fluorine or chlorine, or by nitro, cyano, $C_1$–$C_6$-, in particular, $C_1$–$C_4$-alkyl, $C_1$–$C_6$-, in particular $C_1$–$C_4$-alkoxy and/or trifluoromethyl and $R^3$ represents the radical $-XR^4$ or $-NR^5R_6$, wherein $R^4$ represents $C_{1-10}$-alkyl, $C_{1-4}$-alkoxy-$C_{1-4}$-alkyl, or aryl which has 6 to 10 carbon atoms and is optionally mono-, di-, tri-, tetra- or penta-substituted by identical or different substituents from the group comprising halogen, $C_{1-4}$-alkyl and halogenoalkyl with 1 or 2 carbon atoms and 1 to 5 identical or different halogen atoms, X represents oxygen or sulphur and $R^5$ and $R^6$ are identical or different and represent hydrogen, $C_1$–$C_{10}$-alkyl or aryl which has 6 to 10 carbon atoms and is optionally mono-, di-, tri-, tetra- or penta-substituted by identical or different substituents from the group comprising halogen, $C_1$–$C_4$-alkyl and halogenoalkyl and halogenoalkoxy with in each case 1 or 2 carbon atoms and 1 to 5 identical or different halogen atoms, or $R^5$ and $R^6$, together with the nitrogen atom on which they stand, stand a 5-membered to 7-membered saturated, heterocylic radical, which is optionally substituted by $C_{1-4}$-alkyl and can be interrupted by a further hetero-atom, preferably oxygen.

Particularly preferred compounds of the formula (I) are those
in which $R^1$ and $R^2$ are identical or different and represent $C_1$–$C_6$-alkyl, $C_3$–$C_5$-alkenyl or $C_3$–$C_5$-alkinyl, optionally substituted by methoxy, ethoxy, n- or i-propoxy, methylthio, ethylthio, n- or i-propylthio, fluorine and/or chlorine, or represent $C_5$- or $C_6$-cycloalkyl, optionally substituted by methyl, ethyl, n- or i-propyl or n-, s-, i- or t-butyl, or represent arylalkyl, preferably benzyl or phenethyl, optionally substituted in the aryl part by fluorine, chlorine, nitro, cyano, methyl, ethyl, n- or i-propyl, n-, s-, i- or t-butyl or trifluoromethyl, or represent $C_6$–$C_{10}$-aryl, in particular phenyl or naphthyl, optionally substituted by fluorine, chlorine, nitro, methyl, ethyl, n- or i-propyl, n-, i-, s- or t-butyl, methoxy, ethoxy, n- or i-propoxy and/or trifluoromethyl, and $R^3$ represents the radical $-XR^4$ or $-NR^5R^6$, wherein $R^4$ represents $C_{1-10}$-alkyl, $C_{1-3}$-alkoxy-$C_{1-4}$-alkyl, or phenyl which is optionally mono-, di- or tri-substituted by identical or different substituents from the group comprising chlorine, methyl, ethyl and trihalogenomethyl, X represents oxygen or sulphur and $R^5$ and $R^6$ are identical or different and represent hydrogen, $C_{1-6}$-alkyl, or phenyl which is optionally mono-, di- or tri-substituted by identical or different substituents from the group comprising chlorine, methyl, ethyl, tri-halogenomethyl and trihalogenomethoxy, or $R^5$ and $R^6$, together with the nitrogen atom on which they stand, form a saturated 5-membered to 7-membered heterocyclic radical which is optionally substituted by one or two methyl radicals and can be interrupted by an oxygen atom. Especially preferred compounds of the formula (I) are those
in which $R^1$ represents $C_{1-6}$-alkyl, cyclopentyl, cyclohexyl, or phenyl or benzyl which is optionally mono- or di-substituted by chlorine, methyl, tert.-butyl or trifluoromethyl, $R^2$ represents $C_{1-4}$-alkyl, or phenyl which is optionally mono-, di- or tri-substituted by identical or different substituents from the group comprising methyl, chlorine and iso-propoxy and $R^3$ represents the radical $-XR^4$ or $-NR^5R^6$, wherein $R^4$ represents $C_{1-10}$-alkyl, $C_{1-3}$-alkoxy-$C_{1-4}$-alkyl, or phenyl which is optionally mono-, di- or tri-substituted by identical or different substituents from the group comprising chlorine, methyl, ethyl and trifluoromethyl, X represents oxygen or sulphur, and $R^5$ and $R^6$ are identical or different and represent hydrogen, $C_{1-6}$-alkyl, or phenyl which is optionally mono-, di- or tri-substituted by identical or different substituents from the group comprising chlorine, methyl, ethyl, trifluoromethyl and trifluoromethoxy, or $R^5$ and $R^6$, together with the nitrogen atom on which they stand, represent a morpholine radical, pyrrolidine radical, hexamethyleneimine radical or piperidine radical which is optionally mono- or di-substituted by methyl.

If, in the preparation of the compounds of the formula (I) according to the invention, 4-tolyl N-isocyanatocarbonyl-N-3-methylphenyl-carbamate and pyrrolidine are used as starting components in process variant (a) and N-chlorocarbonyl-N-phenyl-ethylurethane and N,N-di-methyl-urea are used as starting components in process variant (b), the courses of the reactions can be represented by the following equations:

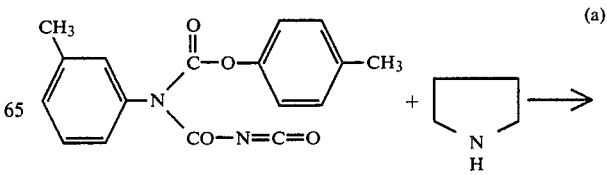

(a)

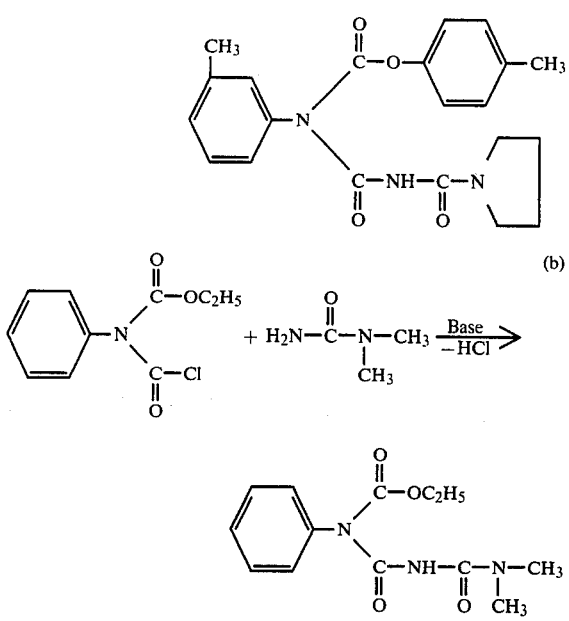

Formula (II) provides a general definition of the N-isocyanatocarbonylcarbamates required as starting substances for the preparation of the compounds of the formula (I) according to the invention. In this formula (II), $R^1$ and $R^2$ have the meanings mentioned above under formula (I). These compounds are known from (U.S. Ser. No. 439,101, filed Nov. 3, 1982, now U.S. Pat. No. 4,482,737, issued Nov. 13, 1984.) preparation, for example from suitable N-substituted carbamic acid esters with chlorocarbonylisocyanate at temperatures between 50° and 200° C. in a solvent. The starting substances of the formula (III), in which $R^3$ and M have the meanings given in the case of formula (I), also required for variant (a) are generally known, commercially available basic chemicals, such as alcohols, thiols or amines.

Formula (IV) provides a general definition of the N-halogenocarbonyl-urethanes to be used as starting compounds in process variant (b), $R^1$ and $R^2$ having the meanings given in the case of formula (I) and Hal representing halogen, preferably chlorine. Most of these compounds are known from (U.S. Ser. No. 416,569, filed Nov. 16, 1973, now U.S. Pat. No. 3,950,367, issued Apr. 13, 1976), and they can be obtained, for example, from iminocarbonic acid esters with phosgene in solvents, such as, for example, cyclohexane, toluene or chlorobenzene, at temperatures between 20° and 120° C. The iminocarbonic acid esters required for this are likewise known (compare, for example, E. Kühle et al., "Angewandte Chemie" 81 (1969) 18 et seq.).

Formula (V) provides a general definition of the substances also required as starting compounds in process variant (b). In this formula, $R^3$ has the meaning given in the case of formula (I). These ureas, carbamic acid esters and thiocarbamic acid esters are generally known compounds. Process variants (a) and (b) according to the invention are preferably carried out in the presence of a solvent or diluent. Virtually all the inert, aprotic organic solvents can be used here. Solvents which can preferably be used as aliphatic or aromatic, optionally halogenated hydrocarbons, such as pentane, hexane, heptane, cyclohexane, benzene, toluene, xylene, methylene chloride, chloroform, carbon tetrachloride, chlorobenzene and dichlorobenzene, ethers, such as diethyl ether, diisopropyl ether, 1,2-dimethoxyethane, tetrahydrofuran and dioxane, esters, such as methyl acetate and ethyl acetate, nitriles, such as acetonitrile and propionitrile, amides, such as dimethylformamide and dimethylacetamide, and dimethylsulphoxide and sulpholane.

The reaction in process (a) according to the invention can be carried out in either the presence or the absence of acid-binding agents. If the reaction is carried out in the presence of acid-binding agents, virtually all the customary acid-binding agents can be used as such acid acceptors.

Acid acceptors which are particularly preferably used are alkali metal and alkaline earth metal hydroxides, such as, for example, sodium hydroxide, potassium hydroxide and calcium hydroxide, alkali metal and alkaline earth metal carbonates or bicarbonates, such as, for example, sodium carbonate or bicarbonate, potassium carbonate and calcium carbonate, and aliphatic, aromatic and heterocyclic amines, such as, for example, trimethyl-, triethyl-, tripropyl- or tributyl-amine, N,N-dimethylbenzylamine, pyridine, 2-methylpyridine, 2,4,6-trimethylpyridine, 2-methyl-5-ethyl-pyridine, diazabicyclooctane (DABCO), diazabicyclononene (DBN) or diazabicycloundecene (DBU).

Process variant (b) is preferably carried out in the presence of one of the abovementioned acid-binding agents.

The reaction temperatures can be varied within a substantial range in processes (a) and (b). In general, the reaction is carried out at temperatures between −50° C. and +200° C., preferably between −20° C. and +150° C.

Processes (a) and (b) are in general carried out under normal pressure.

For carrying out process (a) according to the invention, between 0.8 and 4.0 moles, preferably between 0.9 and 3.0 moles, of starting compound of the formula (III) are in general employed per mole of starting compound of the formula (II). If the reaction is carried out in the presence of acid-binding agents, these are employed in an equivalent amount or in excess, based on the compounds of the formula (II). If no acid-binding agent is used, the reaction is in general carried out by a procedure in which the components are brought together and allowed to react. If the reaction is carried out in the presence of an acid-binding agent, the components are brought together, if necessary with cooling and the reaction mixture is then stirred, if appropriate at elevated temperature. Subsequent working up is effected by customary methods. In general, a procedure, is followed in which the solid residue is filtered off and extracted with an organic solvent and the combined organic phases are washed and concentrated. However, it is also possible to dilute the reaction mixture with water, when the reaction has ended, and to extract the resulting mixture with an organic solvent of low water-miscibility, and to wash and then concentrate the combined organic phases. The products thereby obtained can be freed from any impurities which they still contain by customary measures, such as recrystallization or by a chromatographic route.

The active compounds according to the invention exhibit a powerful microbicidal action and can be employed in practice for combating undesired microorganisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

Some pathogens of fungal and bacterial diseases which fall under the generic terms listed above may be mentioned as examples, but not by way of limitation: Botrytis species, such as, for example, *Botrytis cinerea;* Plasmopara species, such as, for example, *Plasmopara viticola,* Uromyces species, such as, for example, *Uromyces appendiculatus;* Sphaerotheca species, such as, for example, *Sphaerotheca fuliginea; Venturia species, such as, for example, Venturia inaequalis;* Podosphaera species, such as, for example, *Podosphaera leucotricha;* Phytophthora species, such as, for example, *Phytophthora infestans;* Erysiphe species, such as, for example, *Erysiphe graminis;* Puccinia species, such as, for example, *Puccinia recondita;* Fusarium species, such as, for example, *Fusarium culmorum;* Ustilago species, such as, for example, *Ustilago nuda* or *avenae,* Septoria species, such as, for example, *Septoria nodorum;* Tilletia species, such as, for example, *Tilletiacaries;* Xanthomonas species, such as, for example, *Xanthomonas oryzae;* Pseudomonas species, such as for example, *Xanthomonas lachrymans;* Pyricularia species, such as, for example, *Pyricularia oryzae;* Pellicularia species, such as, for example, *Pellicularia sasakii;* Pyrenophora species, such as, for example, *Pyrenophora teres* (conidia form; Drechslera syn: Helminthosporium); Leptosphaeria species, such as, for example, *Leptosphaeria nodorum;* Cochliobolus species, such as, for example, *Cochliobolus sativus* (conidia form: Drechslera, syn: Helminthosporium) and Cercospora species, such as, for example, *Cercospora canescens.*

The good toleration, by plants, of the active compounds, at the concentrations required for combating plant diseases, permits treatment of above-ground parts of plants, of vegetative propagation stock and seeds, and of the soil.

The active compounds can be converted to the customary formulations, such as solutions, emulsions, suspensions, powders, foams, pastes, granules, aerosols, very fine capsules in polymeric substances and in coating compositions for seed, and ULV formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water. By liquefied gaseous extenders or carriers are meant liquids which are gaseous at normal temperature and under normal pressure, for example aerosol propellants, such as halogenated hydrocarbons as well as butane, propane, nitrogen and carbon dioxide. As solid carriers there are suitable: for example ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there are suitable: for example crushed and fractionated natural rocks such as calcite, marble, pumice, sepiolite and dolomite, as well as synthetic granules or inorganic and organic meals, and granules of organic material such as sawdust, coconut shells, corn cobs and tobacco stalks. As emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. As dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations as a mixture with other known active compounds, such as fungicides, insecticides, acaricides, and herbicides, as well as in mixtures with fertilizers and growth regulators.

The active compounds can be used as such or in the form of their formulations or the use forms prepared therefrom, such as ready-to-use solutions, emulsifiable concentrates, emulsions, foams, suspensions, wettable powders, pastes, soluble powders, dusts and granules. They are used in the customary manner, for example by watering, spraying, atomizing, scattering, dusting, foaming, brushing on and the like. It is furthermore possible to apply the active compounds by the ultra-low volume method, or to inject the active compound formulation or the active compound itself into the soil. The seeds of the plants can also be treated.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

Some of the compounds according to the invention also exhibit a selective herbicidal activity or a root-systemic insecticidal activity.

PREPARATION EXAMPLES

EXAMPLE 1

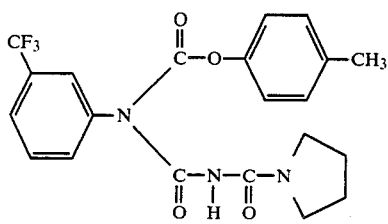

16 g (0.044 mole) of 4-tolyl N-isocyanatocarbonyl-N-3-trifluoromethylphenyl carbamate are dissolved in 100 ml of methylene chloride, and a solution of 31 g (0.044 mole) of pyrrolidine in 50 ml of methylene chloride is added dropwise. When the exothermic reaction has subsided, the mixture is left to stand overnight at room temperature. The cloudy material is then filtered off and the filtrate is evaporated in vacuo. 19.1 g of 4-cresyl $N^2$-pyrrolidinocarbonyl-$N^1$-3-trifluoromethylphenyl-allophanate remain in the form of a colorless viscous oil (quantitative yield) with a refractive index $n_D^{20}$ of 1.5080.

Preparation of the intermediate:

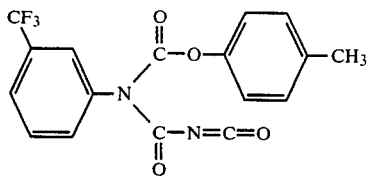

Process according to (U.S. Ser. No. 439,101, filed Nov. 3, 1982, now U.S. Pat. No. 4,482,737, issued Nov. 13, 1984.

145 g (0.49 mole) of 4-tolyl 3-trifluoromethylphenyl carbamate, (melting point 125°–127° C.), obtained from 3-trifluoromethylphenylisocyanate and p-cresol, are suspended in 600 ml of chlorobenzene and the suspension is heated at the boiling point with 58 g (0.55 mole) of chlorocarbonyl isocyanate, with exclusion of moisture, for 7 hours. The solvent is then distilled off in vacuo, after which 171 g (96% of theory) of a yellowish viscous oil remain, which was further reacted directly. Distillation of a sample in a bulb tube oven gave a boiling point of 260° C./0.1 mbar.

The following compounds of the formula (I) are obtained in an analogous manner:

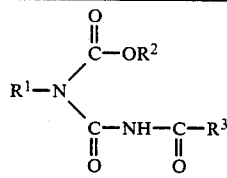

| Example No. | $R^1$ | $R^2$ | $R^3$ | Physical data [melting point °C.; refractive index $n_D^{20}$] |
|---|---|---|---|---|
| 2 | 3-$F_3C$-phenyl | 4-$CH_3$-phenyl | —N(morpholino)O | 102 |
| 3 | 3-$F_3C$-phenyl | 4-$CH_3$-phenyl | —OCH$_3$ | 72 |
| 4 | 3-$F_3C$-phenyl | 4-$CH_3$-phenyl | —OC$_6$H$_{13}$—n | 69 |
| 5 | 3-$F_3C$-phenyl | 4-$CH_3$-phenyl | —OC$_{10}$H$_{21}$—n | 1.4930 |
| 6 | 3-$F_3C$-phenyl | 4-$CH_3$-phenyl | —OCH$_2$CH$_2$OCH$_3$ | 1.5280 |

-continued
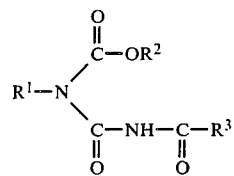
(I)
| Example No. | R¹ | R² | R³ | Physical data [melting point °C.; refractive index $n_D^{20}$] |
|---|---|---|---|---|
| 7 | 3-F₃C-C₆H₄- | C₆H₅- | pyrrolidin-1-yl | 59 |
| 8 | 3-F₃C-C₆H₄- | C₆H₅- | morpholin-4-yl | 121 |
| 9 | 3-F₃C-C₆H₄- | C₆H₅- | —OCH₂CH₂—OCH₃ | 1.5120 |
| 10 | 3-F₃C-C₆H₄- | C₆H₅- | —OC₂H₅ | 1.5100 |
| 11 | 3-F₃C-C₆H₄- | 4-Cl-C₆H₄- | —OCH₃ | 1.5170 |
| 12 | 3-F₃C-C₆H₄- | 4-Cl-C₆H₄- | —OC₂H₅ | 66 |
| 13 | 3-F₃C-C₆H₄- | 4-Cl-C₆H₄- | —OC₄H₉—n | 1.5140 |
| 14 | 3-F₃C-C₆H₄- | 4-Cl-C₆H₄- | —OC₁₀H₂₁—n | highly viscous |
| 15 | 3-F₃C-C₆H₄- | 4-Cl-C₆H₄- | —S-(4-Cl-C₆H₄) | 68 |

-continued
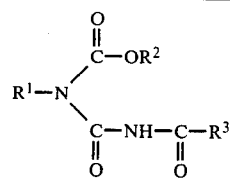
(I)
| Example No. | R¹ | R² | R³ | Physical data [melting point °C.; refractive index $n_D^{20}$] |
|---|---|---|---|---|
| 16 | 3-(F₃C)C₆H₄- | 4-Cl-C₆H₄- | -N(morpholino)O | 155 |
| 17 | 3-(F₃C)C₆H₄- | 4-Cl-C₆H₄- | -NH-C₆H₄-3-CF₃ | 1.5280 |
| 18 | 3-(F₃C)C₆H₄- | 4-Cl-C₆H₄- | -NH-C₆H₄-2-CH₃ | 180 |
| 19 | 3-(F₃C)C₆H₄- | 4-Cl-C₆H₄- | -NH-C₆H₄-4-Cl | 160 |
| 20 | 3-(F₃C)C₆H₄- | 4-Cl-C₆H₄- | -O-C₆H₅ | 150 |
| 21 | 3-(F₃C)C₆H₄- | 4-Cl-C₆H₄- | -NH-C₆H₄-4-OCF₃ | 1.542 |
| 22 | 3-(F₃C)C₆H₄- | 4-Cl-C₆H₄- | $-NH-CH_2-C(CH_3)_3$ | 77 |
| 23 | 3-(F₃C)C₆H₄- | 4-Cl-C₆H₄- | $-NH-C(CH_3)_3$ | 95 |
| 24 | 3,4-Cl₂-C₆H₃- | C₆H₅- | $-NH-C(CH_3)_3$ | 1.505 |

-continued
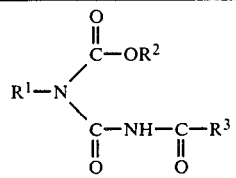
(I)
| Example No. | R¹ | R² | R³ | Physical data [melting point °C.; refractive index $n_D^{20}$] |
|---|---|---|---|---|
| 25 | 3,4-Cl₂-C₆H₃- | C₆H₅- | —NH—CH₂—C(CH₃)₃ | 60 |
| 26 | 3,4-Cl₂-C₆H₃- | C₆H₅- | —NH—C₆H₄—Cl (4-Cl) | 89 |
| 27 | 3,4-Cl₂-C₆H₃- | C₆H₅- | —NH—C₆H₄—CH₃ (2-CH₃) | 165 |
| 28 | 3,4-Cl₂-C₆H₃- | C₆H₅- | —N(C₂H₅)—C₆H₄—Cl (2-Cl) | 87 |
| 29 | 3,4-Cl₂-C₆H₃- | C₆H₅- | —OC₄H₉—n | 108 |
| 30 | 3,4-Cl₂-C₆H₃- | C₆H₅- | —OCH(CH₃)₂ | 143 |
| 31 | 3,4-Cl₂-C₆H₃- | C₆H₅- | —OC₂H₅ | 100 |
| 32 | 3,4-Cl₂-C₆H₃- | C₆H₅- | —OCH₃ | 112 |
| 33 | 3,4-Cl₂-C₆H₃- | C₆H₅- | —N(CH₃)—C₆H₅ | 115 |
| 34 | (CH₃)₃C—CH₂— | C₆H₅- | —N(piperidinyl) | 1.5130 |

-continued

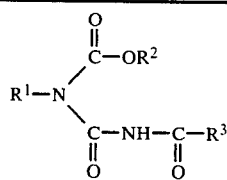
(I)

| Example No. | R¹ | R² | R³ | Physical data [melting point °C.; refractive index $n_D^{20}$] |
|---|---|---|---|---|
| 35 | (CH₃)₃C—CH₂— | —C₆H₄— | —N(CH₂CH₂)₂O (morpholino) | 92–95 |
| 36 | (CH₃)₃C—CH₂— | —C₆H₄— | N(C₂H₅)₂ | 1.5000 |
| 37 | (CH₃)₃C—CH₂— | —C₆H₄— | —OCH₃ | 108–111 |
| 38 | (CH₃)₃C—CH₂— | —C₆H₄— | —OC₆H₁₃—n | 1.4970 |
| 39 | (CH₃)₃C—CH₂— | —C₆H₄— | OCH₂CH₂—OCH₃ | 1.5060 |
| 40 | (CH₃)₃C—CH₂— | —C₆H₄— | —S—C₆H₅ | 100 |
| 41 | (CH₃)₃C—CH₂— | —C₆H₄— | —N(piperidino) | 1.5200 |
| 42 | (CH₃)₃C—CH₂— | —C₆H₄— | —NH—CH₂—C(CH₃)₃ | 1.5050 |
| 43 | (CH₃)₃C—CH₂— | —C₆H₄— | —N(7-Ring, azepane) | highly viscous oil |
| 44 | (CH₃)₃C—CH₂— | —C₆H₄— | —N(pyrrolidino) | 1.5510 |
| 45 | (CH₃)₃C—CH₂— | —C₆H₄— | —N(CH₂CH₂)₂O (morpholino) | 1.5390 |

-continued

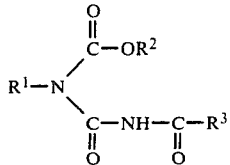
(I)

| Example No. | R¹ | R² | R³ | Physical data [melting point °C.; refractive index $n_D^{20}$] |
|---|---|---|---|---|
| 46 | Cl—CH₂—CH₂— | —⟨phenyl⟩ | —N(C₂H₅)₂ | 1.5170 |
| 47 | Cl—CH₂—CH₂— | —⟨phenyl⟩ | —OCH₃ | 1.5260 |
| 48 | Cl—CH₂—CH₂— | —⟨phenyl⟩ | —OC₆H₁₃—n | 1.5030° |
| 49 | Cl—CH₂—CH₂— | —⟨phenyl⟩ | —OCH₂—CH₂—OCH₃ | 1.5190 |
| 50 | Cl—CH₂—CH₂— | —⟨phenyl⟩ | —N⟨pyrrolidinyl⟩ | 1.5360 |
| 51 | Cl—CH₂—CH₂— | —⟨phenyl⟩ | —NH—CH₂—C(CH₃)₃ | 1.5090 |

The compound shown below is used as a comparison substance in the following examples:

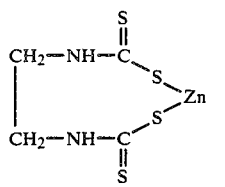

Zinc ethylene-bis-dithiocarbamate

EXAMPLE A

Pyricularia test (rice)/protective
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to preparation Examples 14 and 27.

EXAMPLE B

Pyricularia test (rice)/systemic
Solvent: 12.5 parts by weight of acetone
Emulsifier: 0.3 parts by weight of alkylaryl polyglycol ether To produce a suitable preparation of active compound, 1 part by weight of active compound is mixed with the stated amount of solvent, and the concentrate is diluted with water and the stated amount of emulsifier, to the desired concentration.

To test for systemic properties, standard soil in which young rice plants have been grown is watered with 40 ml of the preparation of active compound. 7 days after the treatment, the plants are inoculated with an aqueous spore suspension of *Pyricularia oryzae*. Thereafter, the plants remain in a greenhouse at a temperature of 25° C. and a relative atmospheric humidity of 100% until they are evaluated.

Evaluation of the disease infestation is carried out 4 days after the inoculation.

In this test, a clearly superior activity compared with the prior art is shown, for example, by the compounds according to preparation Examples 2, 3 4 and 8.

What is claimed is:

1. An allophanate derivative of the formula

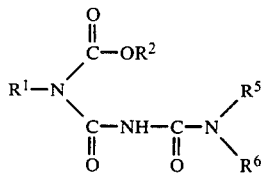

in which
R$^1$ represents C$_5$–C$_{10}$-cycloalkyl, optionally substituted by C$_1$–C$_6$-alkyl, or represents C$_6$–C$_{10}$-aryl, optionally substituted by halogen, nitro, cyano, C$_1$–C$_6$-alkyl, C$_1$–C$_6$-alkoxy and/or trifluoromethyl, R$^2$ represents C$_1$–C$_{10}$-alkyl, C$_2$–C$_{10}$-alkenyl or C$_2$–C$_{10}$-alkinyl, optionally substituted by C$_{1-4}$-alkoxy, C$_{1-4}$-alkylthio and/or halogen, or represents C$_5$–C$_{10}$-cycloalkyl, optionally substituted by C$_1$–C$_6$-alkyl, or represents aralkyl with C$_6$–C$_{10}$ in the aryl part and C$_1$–C$_4$ in the alkyl part, optionally substituted in the aryl part by halogen, nitro, C$_1$–C$_6$-alkyl, cyano and/or trifluoromethyl, or represents C$_6$–C$_{10}$-aryl, optionally substituted by halogen, nitro, cyano, C$_1$–C$_6$-alkyl, C$_1$–C$_6$-alkoxy and/or trifluoromethyl, R$^5$ and R$^6$ are identical or different and represent hydrogen, C$_1$–C$_{10}$-alkyl or aryl which has 6 to 10 carbon atoms, and is optionally mono-, di-, tri-, tetra- or penta-substituted by identical or different substituents from the group comprising halogen, C$_1$–C$_4$-alkyl and halogenoalkyl and halogenoalkoxy with in each case 1 or 2 carbon atoms and 1 to 5 identical or different halogen atoms, or R$^5$ and R$^6$, together with the nitrogen atom on which they stand, represent a 5-membered to 7-membered saturated heterocyclic radical, which is optionally substituted by C$_{1-4}$-alkyl and can be interrupted by a further hetero-atom.

2. An allopanate derivative according to claim 1, in which
R$^1$ represents C$_5$- or C$_6$-cycloalkyl, optionally substituted by methyl, ethyl, n- or i-propyl or n-, s-, i- or t-butyl, or represents phenyl or naphthyl, optionally substituted by fluorine, chlorine, nitro, methyl, ethyl, n- or i-propyl, n-, i-, s- or t-butyl, methoxy, ethoxy, n- or i-propoxy and/or trifluoromethyl, R$^2$ represents C$_1$–C$_6$-alkyl, C$_3$–C$_5$-alkenyl or C$_3$–C$_5$-alkinyl, optionally substituted by methoxy, ethoxy, n- or i-propoxy, methylthio, ethylthio, n- or i-propylthio, fluorine and/or chlorine, or represent C$_5$- or C$_6$-cycloalkyl, optionally substituted by methyl, ethyl, n- or i-propyl or n-, s-, i- or t-butyl, or represent benzyl or phenethyl, optionally substituted in the phenyl part by fluorine, chlorine, nitro, cyano, methyl, n- or i-propyl, n-, s-, i- or t-butyl or trifluoromethyl, or represent phenyl or naphthyl, optionally substituted by fluorine, chlorine, nitro, methyl, ethyl, n- or i-propyl, n-, i-, s- or t-butyl, methoxy, ethoxy, n- or i-propoxy and/or trifluoromethyl, R$^5$ and R$^6$ are identical or different and represent hydrogen, C$_{1-6}$-alkyl, or phenyl which is optionally mono-, di- or tri-substituted by identical or different substituents from the group group consisting of chlorine, methyl, ethyl, tri-halogenomethyl and trihalogenomethoxy, or R$^5$ and R$^6$, together with the nitrogen atom on which they stand, form a saturated 5-membered to 7-membered heterocyclic radical which is optionally substituted by one or two methyl radicals and can be interrupted by an oxygen atom.

3. An allophanate derivative according to claim 1, in which,

R$^1$ represents phenyl which is optionally mono- or di-substituted by chlorine, methyl, tert.-butyl or trifluoromethyl, R$^2$ represents C$_{1-4}$-alkyl, or phenyl which is optionally mono-, di- or tri-substituted by identical or different substituents from the group consisting of methyl, chlorine and iso-propoxy and R$^5$ and R$^6$ are identical or different and represent hydrogen, C$_{1-6}$-alkyl, or phenyl which is optionally mono-, di- or tri-substituted by identical or different substituents from the group consisting of chlorine, methyl, ethyl, tri-fluoromethyl and trifluoromethoxy, or R$^5$ and R$^6$, together with the nitrogen atom on which they stand, represent a morpholine radical, pyrrolidine radical, hexamethyleneimide radical or piperidine radical which is optionally mono- or di-substituted by methyl.

4. A compound according to claim 1, wherein such compound is 4-tolyl N$^2$-morpholinocarbonyl-N$^1$-3-trifluoromethyl-phenyl-allophanate of the formula

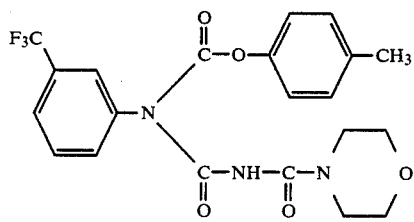

5. A compound according to claim 1, wherein such compound is phenyl N$^2$-morpholinocarbonyl-N$^1$-3-trifluoromethyl-phenyl-allophanate of the formula

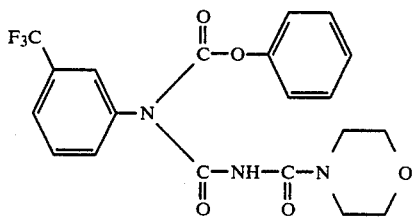

6. A compound according to claim 1, wherein such compound is phenyl N$^1$-(3,4-dichloro-phenyl)-N$^2$-(2-methyl-anilinocarbonyl)-allophanate of the formula

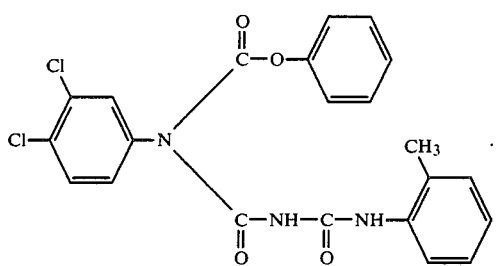

7. A fungicidal composition comprising a fungicidally effective amount of a compound according to claim 1 in admixture with a diluent.

8. A method of combating fungi which comprises applying to such fungi or to a fungus habitat a fungicidally effective amount of a compound according to claim 1.

9. The method according to claim 8, wherein such compound is
4-cresyl $N^2$-morpholinocarbonyl-$N^1$-3-trifluoromethyl-phenyl-allophanate,
phenyl $N^2$-morpholinocarbonyl-$N^1$-3-trifluoromethyl-phenyl-allophanate or
phenyl $N^1$-(3,4-dichloro-phenyl)-$N^2$-(2-methyl-anilinocarbonyl)-allophanate.

* * * * *